US008224426B2

(12) United States Patent
Lilge et al.

(10) Patent No.: US 8,224,426 B2
(45) Date of Patent: Jul. 17, 2012

(54) OPTICAL TRANSILLUMINATION AND REFLECTANCE SPECTROSCOPY TO QUANTIFY DISEASE RISK

(75) Inventors: Lothar Lilge, Toronto (CA); Brian C. Wilson, Toronto (CA); Michelle K. Nielsen, Toronto (CA)

(73) Assignee: University Health Network, Toronto (CA)

( * ) Notice: Subject to any disclaimer, the term of this patent is extended or adjusted under 35 U.S.C. 154(b) by 2042 days.

(21) Appl. No.: 10/496,108

(22) PCT Filed: Nov. 20, 2002

(86) PCT No.: PCT/CA02/01771
§ 371 (c)(1),
(2), (4) Date: Jun. 27, 2005

(87) PCT Pub. No.: WO03/043492
PCT Pub. Date: May 30, 2003

(65) Prior Publication Data
US 2006/0173352 A1    Aug. 3, 2006

(51) Int. Cl.
*A61B 6/00*    (2006.01)
(52) U.S. Cl. ......... 600/476; 600/407; 600/309; 600/310
(58) Field of Classification Search ............ 600/407, 600/476, 309, 310
See application file for complete search history.

(56) References Cited

U.S. PATENT DOCUMENTS
6,095,982 A    8/2000    Richards-Kortum et al.

OTHER PUBLICATIONS
Egan and Dolan "Optical Spectroscopy. Pre-mammography marker", ACTA RADIOLOGICA, vol. 29, No. 5, 1998, pp. 497-503.

*Primary Examiner* — Brian Casler
*Assistant Examiner* — Nasir S Shahrestani
(74) *Attorney, Agent, or Firm* — Hill & Schumacher; Lynn C. Schumacher

(57)    ABSTRACT

The present invention uses spectroscopic tissue volume measurements using non-ionizing radiation to detect pre-disease transformations in the tissue, which increase the risk for this disease in mammals. The method comprises illuminating a volume of selected tissue of a mammal with light having wavelengths covering a pre-selected spectral range, detecting light transmitted through, or reflected from, the volume of selected tissue, and obtaining a spectrum of the detected light. The spectrum of detected light is then represented by one or more basis spectral components, an error term, and an associated scalar coefficient for each of the basis spectral components. The associated scalar coefficient is calculated by minimizing the error term. The associated scalar coefficient of the each of the basis spectral components is correlated with a pre-selected property of the selected tissue known to be indicative of susceptibility of the tissue for the pre-selected disease to obtain the susceptibility for the mammal to developing the pre-selected disease.

24 Claims, 15 Drawing Sheets

OPTICAL TRANSILLUMINATION AND REFLECTANCE SPECTROSCOPY TO QUANTIFY DISEASE RISK

CROSS REFERENCE TO RELATED UNITED STATES PATENT APPLICATION

This patent application is a National Phase application claiming the benefit of PCT/CA02/01771 filed on Nov. 20, 2002; which further claims priority benefit of U.S. provisional patent application, Ser. No. 60/331,633, filed on Nov. 20, 2001, entitled OPTICAL TRANSILLUMINATION SPECTROSCOPY TO QUANTIFY DISEASE RISK.

FIELD OF THE INVENTION

The present invention relates to the use of optical transillumination/reflectance spectroscopy as a diagnostic for determination of the risk for diseases.

BACKGROUND OF THE INVENTION

As early cancer or disease detection and diagnosis make further inroads into clinical practice, the high cost of current disease screening techniques redirected the focus of the investigators towards methods capable of quantifying the risk towards these diseases as a practical pre-screening tool. One particular application area is epidemiological science and public health research into cancer prevention, so the invention is applicable for a wide variety of chronic or slowly developing diseases such as Alzheimer's, or Multiple Sclerosis. However, prevention required identification of the population at risk in association with an appropriate prevention or risk reduction intervention for example through the control of disease inducing agents or lifestyle changes (exercise, diet etc.) An example risk quantification is the work related to assessing the breast cancer risk in the general population or subgroups thereof by Boyd, Yaffe et al. (1-3) which showed that X-ray density patterns are identified as having one of the highest odds ratios towards the risk of breast cancer between the low risk and the high risk groups. For the specific case of breast cancer, radiologically dense breast tissue on mammography indicates the presence of stromal and epithelial tissue in the breast, the amount of which is strongly related to risk of breast cancer, with increasing amount of radiologically dense tissue related to increased risk. The ability to assess the breast cancer risk enables new steps in cancer prevention, for example through lifestyle and dietary changes (4).

One of the major disadvantages of the current standard for Breast Cancer Risk assessment is the use of ionizing radiation. This results in the late introduction of this diagnostic modality during the life of a woman, due to the inherent risk when using ionizing radiation in a diagnostic modality. Other good risk predictors are in general also only available once a woman has reached around 40 years of age, such as cancer incidence in first degree relatives (mother and sisters). However, the late onset in using these risk assessment modality will reduce the available time frame for any intervention aimed at reducing the disease risk. Hence, there is a clear need for a non-ionizing modality which can be employed in young patients, here in post puberty pre-menopausal women.

Non-ionizing radiation was employed in various optical mammography approaches, usually in attempts to image the breast, and to detect breast lesions (5,6) commonly using frequency domain technologies at only a few specialized wavelengths, or as spectroscopic approaches for the determining the tissue optical properties of normal versus malignant breast tissue (7). These spectroscopic applications, including an article by Egan and Dolen (8) are rather intended for determination of the probability for the presence of cancer, but do not address the concept of risk assessment, e.g. as a pre-screening tool.

U.S. Pat. No. 6,121,775 is directed to an MRI imaging method and apparatus and provides a physical interrogation methods related to detecting small changes in tissue.

U.S. Pat. No. 5,079,698 is directed to a transillumination method and apparatus for the diagnosis of breast tumors and other breast lesions by normalization of an electronic image of the breast. U.S. Pat. No. 6,002,958 is directed to a method and apparatus for diagnostics of internal organs. This patent teaches the use of NIR radiation in the 0.6-1.5 um wavelength range and adds ultrasound to the analysis tools. These two patents specifically create images of the organ U.S. Pat. No. 6,095,982 discloses a spectroscopic method and apparatus for optically detecting abnormal mammalian epithelial tissue' covers only Raman and fluorescence methods. U.S. Pat. No. 6,069,689 discloses an apparatus and methods relating to optical systems for diagnosis of skin diseases while very generally written and addressing, reflectance, fluorescence and Raman, using a plurality of light emitting diodes. While some changes in the tissue (skin) are mentioned the idea of risk assessment is not included in this or any other patent related to the use of non-ionizing radiation.

SUMMARY OF THE INVENTION

The present invention uses spectroscopic tissue volume measurements using non-ionizing radiation to detect pre-disease transformations in the tissue, which increase the individuals risk for this disease.

In one aspect of the present invention there is provided a method for assessing susceptibility for developing a pre-selected disease in a mammal, comprising:

a) illuminating a volume of selected tissue of a mammal with light having wavelengths covering a pre-selected spectral range;

b) detecting light transmitted through, or reflected from, said volume of selected tissue, and obtaining a spectrum of said detected light;

c) representing the spectrum of detected light by a set of basis spectral components, an error term, and an associated scalar coefficient for each basis spectral component in said set, the set of basis spectral components including at least one basis spectral component, the associated scalar coefficient for each basis spectral component being calculated by minimizing the error term; and d) correlating the associated scalar coefficient for each spectral component with a pre-selected property of the selected tissue known to be indicative of susceptibility of the tissue for the pre-selected disease to obtain the susceptibility for the mammal to developing the pre selected disease.

In another aspect of the invention there is provided an apparatus for assessing susceptibility for developing a pre-selected disease in a mammal, comprising:

a) holder means for holding and immobilizing an anatomical part of a mammal containing tissue to be optically probed;

b) light source means for illuminating a volume of selected tissue of a mammal with light having wavelengths covering a pre-selected spectral range;

c) detection means for detecting light transmitted through, or reflected from, said volume of selected tissue;

d) computer control means connected to said detection means for producing a spectrum of said detected light from an output of said detection mean, the computer control means including processing means for representing the spectrum of detected light by a set of basis spectral components, an error term, and an associated scalar coefficient for each spectral component in said set, the set of basis spectral components including at least one basis spectral component, the associated scalar coefficient for each basis spectral component being calculated by minimizing the error term, the processing means includes means for correlating the associated scalar coefficient for each basis spectral component with a pre-selected property of the selected tissue known to be indicative of susceptibility of the tissue for the pre-selected disease to obtain the susceptibility for the mammal to developing the pre-selected disease, the computer control means including display means for displaying the susceptibility.

BRIEF DESCRIPTION OF THE DRAWINGS

The method and apparatus constructed in accordance with the present invention will now be described, by way of example only, reference being had to the accompanying drawings, in which.

DETAILED DESCRIPTION OF THE INVENTION

Figure 1:
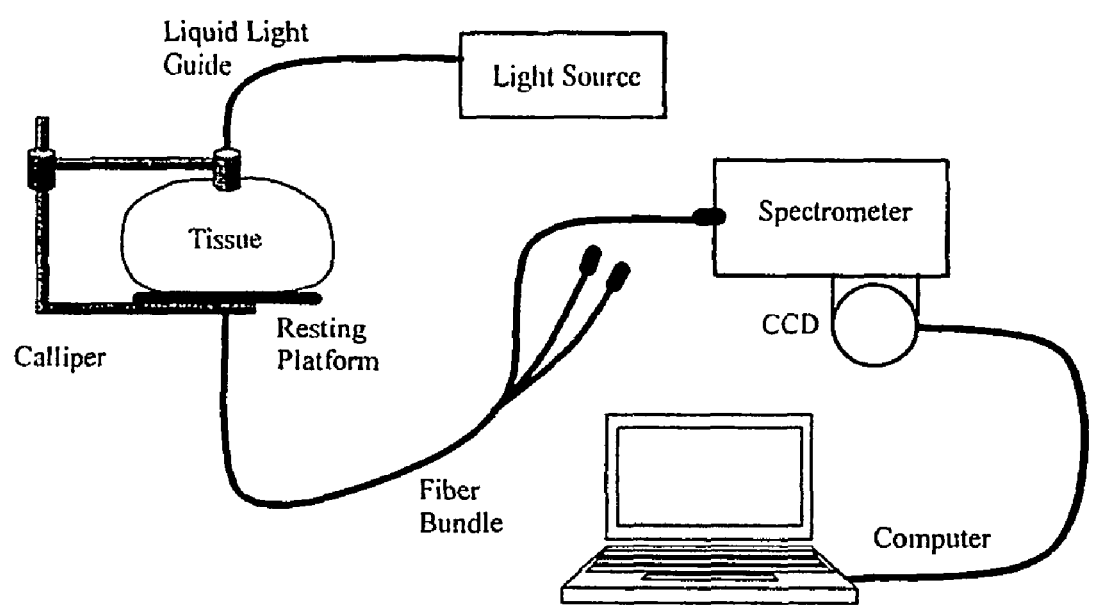
FIG. 1 shows the block diagram of one possible embodiment of an apparatus produced in accordance with the present invention.

Referring to FIG. 1 shows an apparatus 10 used in the present invention comprises a light source 12, waveband selection devices, delivery optical fibre 14, tissue support 16, collection optical fibre bundle 18, wavelength dispersing element, opto-electronic detector 20 and CPU 22. Spectra can be corrected for the wavelength dependent transfer function of the instrument and the physical interoptode distance. It will be understood that this is not required as it can also be convoluted into the numerical correlation analysis. Additionally, the optical fibre 14, the tissue support and the optical fibre bundle is optional. The wavelength selective device can be either prior to or post the interrogated tissue.

For use in studies related to breast tissue, the light source 12 was a 12 Watt halogen lamp (Welch Allyn) with stabilized power supply serving as a broadband light source. The ultraviolet to green and mid infrared radiation were eliminated using a cut-off filter (at 500 nm) and a heat filter, respectively. The remaining light was coupled into a 5 mm diameter liquid light guide, which served as the source fiber in contact with the skin on the top of the breast. A total power of 0.25 Watt, covering the 550-1300 nm bandwidth, was delivered to the skin surface. The holder of the source fiber and the plate in which the detector fiber was embedded were made of black plastic to absorb reemitted photons. The source fiber was in firm contact with the tissue and slightly compressed it by 5 mm. The source and detector fibers (optodes) were held coaxially, pointing towards each other, via a custom-made calliper attached to the resting platform. The calliper allowed the measurement of the inter-optode distance (cm) and hence, the physical thickness of the interrogated tissue. Transmitted light was collected via a custom-made 7 mm diameter fiber bundle (P&P Optical Kitchener, Ontario, Canada). Wavelength resolved detection in the visible-near infrared was achieved using a holographic transillumination grating (15.7 rules/mm blazed at 850 nm) (Kaiser, Calif., USA) and a 2D, cryogenically-cooled silicon CCD (Photometrics, New Jersey, USA) at a spectral resolution of less than 3 nm between 625 nm and 1060 nm. This spectral resolution was achieved by positioning a 0.5 mm slit between the distal end of the collection fiber and the spectral grating. The peak quantum efficiency (>0.8) of the detector was at 780 nm, falling to 0.2 at 1100 nm. By imaging the entrance slit of the spectrograph onto the 2D CCD, 50 rows of pixels were effectively exposed to detected light, thus increasing the dynamic range of the electronic detection by up to 50 times. To minimized background noise, cryogenic cooling reduces the dark counts to ~0.06 electrons per hour. Further noise reduction was achieved using exposure times of 2-3 seconds and averaging up to five scans. The system's dynamic range was >5 OD (optical densities) with a signal-to-noise ratio of >$10^4$ at peak sensitivity and >10 across the remaining bandwidth of the system.

In order to collect the transmitted light emerging from the tissue, a wavelength dispersing medium (in the preferred embodiment a grating) for the various wavelength ranges use, if present, and an opto-electronic detector, here a Si based (0.65 μm to 1.5 μm) photodiode array (PDAs) are used. The PDA's information is transferred directly or delayed to the computer containing a numerical analysis program to quantify the disease risk using a previously trained algorithm. The correlation between spectral data and disease risk is based on the spectral attenuation, through photon absorption and scattering, only. The particular disease risk assessment system comprises in its current version a continuous optical spectrum with wavelength in the 550 nm to 1000 nm range.

Different embodiments of the apparatus may include an InGaAs based (0.9 μm to 1.7 μm), or equivalent opto-electronic detector to cover also the longer wavelength range which is transmitted through tissue, or can comprise also only various wavelengths or wavelength bands within the VIS/NIR range, such as attainable with filters of direct emission devices with limited bandwidth such as laser, LED or similar.

In another embodiment of the apparatus there is included at least a single (whereas three is preferred) wavelength, frequency domain transillumination system, spanning most of the steady state wavelength range for transillumination. In one non-limiting embodiment the three wavelengths may be 785, 808, 905 nm. The lasers in the frequency domain system need to be modulated between 10 to 400 MHz (215 MHz in the present system) to obtain a good phase shift resolution for 5 cm physical pathlength between delivery and detection optode. The system should provide a phase shift resolution of better than 20. The lasers used here provide ~200 mW average power at the distal end of the delivery fibers in contact with the patient. Intensity modulation is achieved by modulating the driving current of the lasers via a biased-T, a method to recapture the transmitted light and guide it to the PMT with fast time response, a preamplifier filtered to the appropriate modulation frequency, a lock-in detection to quantify the demodulation and the phase shift compared to a standard either from the laser driver current or a portion of the light prior to entering the tissue, and a data transfer system to a computer to translate the phase shift and demodulation data into a differential path length factor and scattering coefficient. In frequency domain measurements various modi operandi can be employed one being heterodyne detection technique, which can use also very lower power lasers. Other methods to quantify the optical pathlength are described (10, 11) and include time resolved detection or time resolved single photon detection.

The ability to quantify disease risk and hence the population members at risk can be increased through additional measurements such as skin reflectance measurements to be able to subtract the skin contribution to the optical transillumination spectrum, so clearly this information may not be required. Depending on the part of the body being diagnosed additional components such as anatomical supports may be included, for example if the breasts are being studied, a support stand for the breast, and a holder for the liquid light guide and optical fibres for light delivery, and a random fibre bundle for light collection. The latter may be a trifurcated fibre bundle to deliver transmitted photons to the PMT (frequency domain measurements), Si-based and InGaAs-based PDAs respectively. Again these are to a large extent optional, for example one can envision a cup like device which holds the sources and detectors in direct contact with the tissue. A means to measure the angle and distance between the delivery and detection optodes equivalent to the physical tissue thickness or in the case of a reflectance measurement the interoptode distance as the latter will determine the tissue depth most likely interrogated by the photons. It is noted that the inventors have shown some correlation and predictive abilities with thickness correction of the data. Software to extract spectral absorption and light scattering features to quantify the risk for a specific disease is loaded onto the CPU. Software was trained using data from clinical studies providing the optical spectra and an independent measure of the risk as discussed hereinafter.

In order to correct for variations in the wavelength dependent signal transfer function of the system, all transillumination spectra were referenced to a daily collected transmission standard made of 1 cm thick, ultra-high density polyurethane (Gigahertz Optics, Munich, Germany). All measured spectra are thus given as wavelength dependent (rel OD). This referencing to a known standard yields a universal applicable dataset and hence the subsequent developed mathematical models correlating transillumination spectra with risk will also become universally valid, that is independent of the actual instrument used to collect the data.

The spectral volume measurements can be augmented by adding extended long wavelength (comprising the NIR range transmitted through tissue, e.g. up to 1.7 μm) and frequency domain measurements. The former providing more information about vibrational bands of the biomolecules in the interrogated volume. The latter enables by using a limited number of wavelengths (3 or more), to determine the differential pathlength factors of the tissue (6). Combining this with the transillumination spectra allows one to obtain absolute absorption spectra and subsequently derivation of the contributions of various chromophores responsible for the absorption spectra measured providing additional information for the identification of the population at risk and also insight into the molecular changes associated with or resulting from the tissue transformation.

Analysis of Reflectance or Transillumination Optical Data for Assessment of Disease Risk The following describes four nonlimiting examples of mathematical modelling techniques capable of establishing a correlation between the optical spectra and a particular outcome, in the present case risk of disease. This is not a complete or comprehensive list of all the methods available which may be used and other methods such as hybrid linear analysis (12) are available and persons skilled in this type of analysis can identify other methods. These spectral analysis techniques have been used extensively in chemometrics field to solve for the concentration of a constituent of interest without knowing the spectra of all constituents present in a chemical sample (13) or where multiple chemicals of interest have overlapping spectra, (14). These analysis techniques construct models that identify the variance within the spectral data set or, when trained with a known range of concentrations, can identify the variance that is relevant to the constituent(s) of interest. Through training the model derives component spectra that resemble the constituent spectra within the sample, and can later be used to predict the concentrations of constituents from new sample spectra. However, these component spectra may not have direct physical meaning but can represent the spectral features of the pure constituent spectra.

In the case of breast cancer which is exemplified hereinafter, it has been shown by Thompson and Tatman (9) that the tissue composition will change slowly as the breast is undergoing sequential changes towards dysplasia, carcinoma in situ and then invasive cancer, often involving or resulting in concentration change of different optically (light absorption or fluorescence) active molecules and/or structures (light scattering).

In the specific case of breast cancer the idea is based on the fact that the same structures and chemicals, that give rise to the x-ray attenuation, the current (gold) standard for breast cancer risk assessment, will also result in changes in the transillumination spectra. These changes will be evident in the attenuation and/or scattering of the visible/NIR light due to different contributions of the optically active molecules. Correlation between the x-ray mammography and the spectral transillumination information can be established and quantified by a variety of different numerical methods, among which are principal component analysis or linear discriminate analysis when the breast density based on mammographic analysis is provided as classification (nominal data) or using partial least squares or principle component regression when the mammographic analysis is provided as % dense tissue (interval data). Besides x-ray mammographic analysis, other methods which may be used to obtain the parenchymal breast tissue density may include ultrasound, computed tomography, cone beam computed tomography, electrical impedance spectroscopy and magnetic resonance imaging.

Principal Component Analysis (PCA) and Linear Discriminant Analysis (LDA)

PCA is optimized for comparison of vectors with nominal data, in this case correlating spectra to the density classification, thereby making use of the complete spectral information while reducing the dataset size. For this, PCA determines the amount of variance within the test group of spectra and uses it to iteratively reduce the dataset to representative spectra, called components. The spectral data are represented by a smaller number of vectors in a lower dimensional space while still including the maximum amount of variance within the data set. (15). This is accomplished by solving for the covariance or correlation matrix of the data matrix X (m×n) comprised of the dataset of all spectra obtained (n) and the spectral range monitored (m), such that:

$$cov(X) = \frac{X^T X}{n-1} \quad (1)$$

PCA decomposes the data matrix X as the sum of the outer products of the vectors $t_i$ and $p_i$ and a residual matrix E:

$$X = t_1 p^T_1 + t_2 p^T_2 + t_3 p^T_3 + \ldots + t_i p^T_i + E$$

or $$X = TP^T + E \quad (2)$$

Where the elements of the $t_i$ (n×1) vectors are the scores that contain information on how the spectra relate to each other, and the $p_i$ vectors (m×1) or components are the eigenvectors of the covariance matrix and show how the selected variance relates to each other. The components $p_i$ are eigenvectors of the covariance matrix, so that $$cov(X) p_i = \lambda_i p_i \quad (3)$$

where $\lambda_i$ is the eigenvalue associated with the eigenvector $p_i$.

Also for any X and $t_i$ and $p_i$ pair X $p_i = t_i$ (i.e. the score vector $t_i$ is the linear combination or representation of the original X defined by $p_i$). It is generally found that data can be described in fewer components $p_i$ than original variables (m) and that the components can be combinations of variables that are useful descriptions of particular constituents in the tissue. As stated above, the shape of the useful components will be a combination of spectral signatures of chromophores that vary with tissue density. Scores (elements of $t_i$) that differentiate between tissue densities identify useful components ($p_i$).

The scores (elements of $t_i$) can be graphically plotted against one another to show any potential clustering of spectra that are related. In this study PCA was calculated on the test set (⅔ of available spectra) and the same mathematical model, e.g. retaining the $p_i$ was used to predict the scores $t_i$ on the validation set (⅓ spectra).

Linear Discriminant Analysis (LDA) was used on the PCA scores to enhance the differentiation between the two extreme nominal categories (low vs high density). LDA finds a discriminant rule for defined groups within the dataset. It is based on drawing the boundary halfway between the means on a pair wise basis (adjusted slightly if there is some prior probability of group identity). It calculates the discriminant rule by computing optimizing factors (criterion $_j$) that are based on the covariance matrix of the given groups. The targets that are used for training identify the density category group (16)

$$criterion_j = inv(cov X_j) \cdot S_b \quad (4)$$

Where j is the particular group and $S_b$ is the between class variance defined by $$S_b = \sum_j (x_j - \overline{x_n})^2 \quad (5)$$

In this study, the LDA algorithm was trained using the training dataset by leaving one spectrum out during each training run and then predicting it's tissue density group. The rest of the spectra from the validation set were then classified using the trained model. The LDA scores can also be plotted in a similar cluster diagram as the PCA scores (16) Table 1 shows the key to differences between PCA and LDA.

Statistical significance for the PCA and LDA prediction was established using measures similar to sensitivity and specificity values commonly used to evaluate the validity of diagnostic tests. As transillumination is currently envisioned as a method for identifying those women with high tissue density within the entire population, increased HDM is preferable over increased LDM. Consequently, a high density measure (HDM) was used to assess the quality of the prediction model. HDM was defined as the ratio of those women that were predicted to have high density tissue with the optical transillumination method to those who were categorized as having high tissue density by the Radiologist. Conversely, the low density measure (LDM) is a measure of the ability to correctly identify those spectra that do not have high density.

TABLE 1

Properties of Principal Component Analysis and Linear Discriminant Analysis.

| | PCA | LDA |
| --- | --- | --- |
| Input data | Spectral vector | Requires PCA scores as input |

TABLE 1-continued

Properties of Principal Component Analysis
and Linear Discriminant Analysis.

|  | PCA | LDA |
|---|---|---|
| Result space size e.g. classifications | Undefined since # of PC's is undefined | Defined by training procedures |
| Data reduction | Vector->scalar | Scalar->scalar |
| Training or Density readings needed | No | Yes |
| Presentation of output data | Relationship of scalars by cluster analysis | Relationship of scalars by categories or cluster analysis |
| What variance is used | Those captured in principal components | The variance between the defined groups |
| Additional output information | Component vectors contain physical meaning | Discriminant rule no apparent physical meaning |

Figure 2:
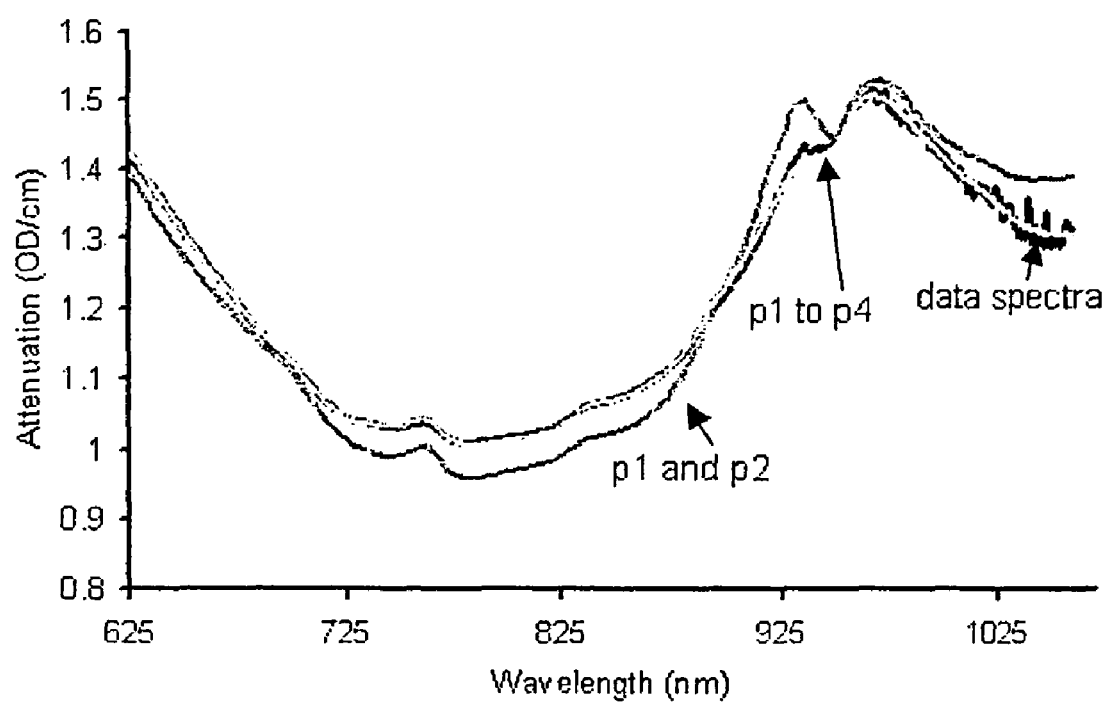
FIG. 2 show a reconstruction of an experimentally obtained optical transillumination spectrum by a linear combination of either only the first two or four principle components.

FIG. 2 shows a reconstruction of an experimentally obtained spectrum by either only two or four principle components.

Principal Component Regression and Partial Least Squares Analysis

PCR and PLS are analysis techniques are optimized for comparison of vector inputs with interval target data. For this case the spectra are compared to the percent density readings. Statistical significance was established using the Pearson correlation coefficient as well as the slope and intercept of the regression line. Both PCR and PLS analysis require training and perform regression analysis on the dataset, but use different types of variance identification to predict the target variable, in this study the percent density read from the mammogram, see Table 2.

As a first attempt for solving for a concentration of a constituent, Inverse Least Squares analysis has been used for well behaved data, where spectral features are not overlapped and predictions of the constituent is not effected by collinearity problems with other constituents in the sample. Here Y is defined as:

$$Y = Xb \quad (6)$$

Where b is the regression vector that is found by solving for the pseudoinverse of X. This cannot be used here since all the spectral features contributing to the spectral shape and that lead to density prediction are not defined so there could be collinearity problems.

Principle Component Regression calculates principal components in a similar manner to Principal Component Analysis and then performs regression analysis of the scores matrix with the known targets or tissue densities from the training set. It does this by solving the following equation $$Y = (PT^T)b \quad (7)$$

$$\text{where } b = P(T^T T)^{-1} T^T Y \quad (8)$$

which is similar for Inverse Least Squares analysis above in equation 7, except that $X = PT^T$. The regression vector b is the least squares solution for T, where T are scores from the PCA and T is a (n×k) matrix, where n is the number of spectra and k is the number of factors used in the model. Y is the (n×1) vector of targets, in this case percent density of the region of interest of the mammogram (17).

For Partial Least Squares Analysis, the basis vectors or latent variables (equivalent to the principal components) are extracted using the related targets, such as percent density, by solving equation 7 and relating b to the targets directly by solving:

$$b = W(P^T W)^{-1}(T^T T)^{-1} T^T Y \quad (9)$$

where W is a weighting vector that relates the target set (prediction values) with the variance in the dataset during the decomposition into factors. This allows the PLS algorithm to solve for components that are correlated with the targets (Y) while describing a large amount of the variation in X. (17) For a more detailed explanation please see Kowalski B R and Geladi P (1986), (17) Wise B M (2000), (15) and Haaland D M and Thomas E V (1988). (14).

With both PCR and PLS only a single regression vector b is used in subsequent predictions of spectra. This b vector is selected by calculating the predicted residual error sum of squares (PRESS) value for each $b_i$ using the training set. The chosen b vector has the fewest number of iterations (lowest value of i) and the lowest PRESS value when the training set is used to establish the model.

TABLE 2

Properties of Principal Component Regression
and Partial Least Squares Analysis.

|  | PCR | PLS |
|---|---|---|
| Inputs | Density (targets) and spectra for a training set | Density (targets) and spectra for a training set |
| Data reduction | No | No |
| Density readings needed | For each spectrum in training set | For each spectrum in training set |
| Presentation of output data | Estimated percent density | Estimated percent density |
| What variance is used | Those captured in principal components | The variance that matches the targets |
| Additional output info | b vector | b vector |

In this study the PRESS values were calculated for both PCR and PLS for the training sets, using the built-in cross-validation function in Matlab 6.0 PLS toolbox. The b vector with the lowest PRESS value was selected. The training set was randomized and split into four sections, the respective algorithms were then trained by a Venetian blind method with four repeats. The subsequent b vectors were then averaged and used to predict the tissue density for entire training set and subsequently the validation set.

The method disclosed herein will now be described with a nonlimiting example of study in breast tissue.

EXAMPLE

Breast Tissue Transillumination Study

Transillumination spectroscopy measurements were taken in a dark room with the volunteer seated comfortably, and the breast resting on a horizontal support (FIG. 1). Total data acquisition time was approximately 15 minutes allowing measurements at all 8 positions and necessary re-positioning of the optodes. There was little discomfort to the volunteers due to point compression of the breast by the source optode.

Figure 3:
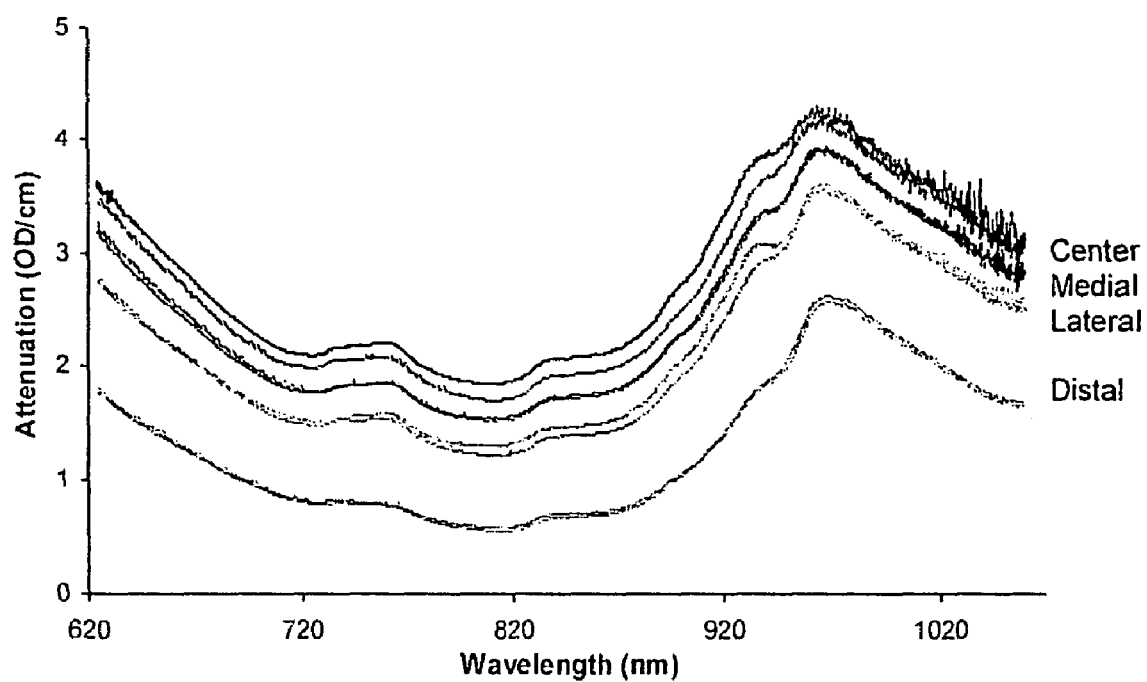
FIG. 3 shows an example of a typical set of measurements comprised of eight spectra from a volunteer representing the four quadrant of the breast on either side of the bilateral organ.

FIG. 3 shows an example of a typical set of measurements comprised of eight spectra from the volunteer. Spectra from the respective bilateral positions of the breast show symmetry, as expected in women with healthy breast tissue. In previous studies, this criterion of spectral symmetry in the same position of both breasts was used, by Egan and Dolan, to indicate absence of breast cancer in the examined areas (8). The reproducibility of the optical transillumination measurements within one visit was analyzed by recruiting a volunteer to undergo multiple procedures.

A total of 8 spectra were collected per volunteer representing the four quadrants (medial, distal, lateral and central) of both breasts. These spectra can be further pre-processed by correcting for tissue thickness (OD/cm) and/or auto-scaling prior to development and testing of the mathematical models used to then correlate with tissue density. In general for Principal Component Analysis and similar models, scaling is used if the input variables have different units or if there are large deviations in some input variables compared to other variables within the data set.

For auto-scaling, the data was mean-centered, where the mean optical density value of the data set at each wavelength was subtracted from all spectra, and scaled to one unit variance by dividing all the values at each wavelength by the standard deviation for that wavelength. This was applied only to the training set data for PCA models developed, whereas scaling of the validation set the previous obtained mean and standard deviation vectors were used. See Table 3 for pre-processing options used for the interpretation of the spectral data set.

TABLE 3

Pre-processing techniques of the spectral dataset and a reference number used in future sections.
Pre-processing of Dataset

| | |
|---|---|
| Transfer function corrected | I |
| Thickness and transfer function corrected | II |
| Autoscaled and transfer function corrected | III |
| Autoscaled and thickness and transfer function corrected | IV |

A detailed example of establishing a correlation between optical spectra and disease risk follows for the example of PCA. It is generally found that data can be described in fewer components $p_i$ than original variables (m=436 wavelength elements) and that the components can be combinations of variables that are useful descriptions of particular constituents in the tissue. As stated above, the shape of the useful components will be a combination of spectral signatures of chromophores that vary with tissue density. Scores (elements of $t_i$) that differentiate between tissue densities identify useful components ($p_i$). The scores (elements of $t_i$) can be graphically plotted against one another to show any potential clustering of spectra that are related. Here the PCA algorithm was trained on a test set (n=544 spectra) and the same mathematical model, i.e. retaining the $p_i$, was used to predict the scores $t_i$ on the validation set (n=192 spectra).

Statistical significance for the PCA prediction was established using high density measure (HDM) as it is preferable over increased low density measure (LDM) both are similar to sensitivity and specificity. As transillumination is envisioned as a method for identifying women with high tissue density within the entire population, improved HDM is desired.

Consequently, HDM was used to assess the quality of the prediction model defined as the ratio of women predicted to have high density tissue to those who were categorized as having high tissue density by the radiologist. LDM is a measure of the ability to correctly identify those spectra that do not have high density.

Figure 4:
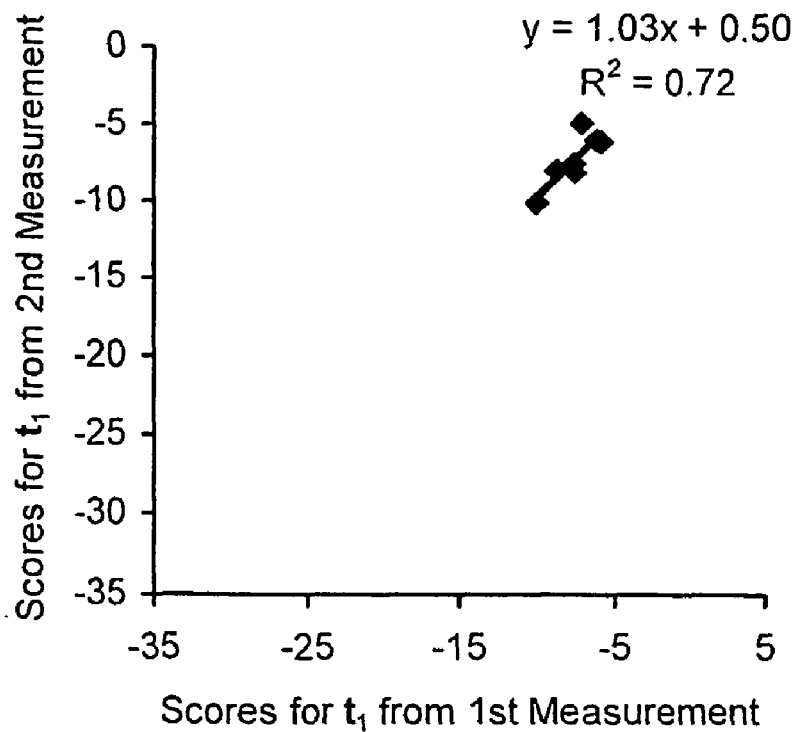
FIG. 4 shows the correlation of the $t_1$ and $t_2$ scores from the spectra that were repeatedly measured resulting in a regression slope and correlation coefficient close to unity.
Figure 4:
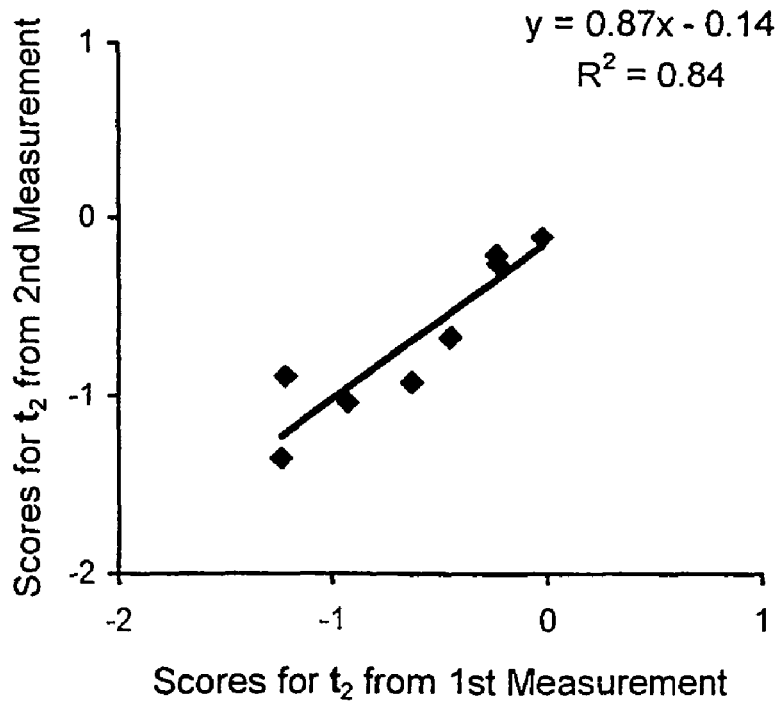

FIG. 4 shows the correlation of the $t_1$ and $t_2$ scores from the spectra that were repeatedly measured. FIG. 4 also shows acceptable reproducibility with slopes of the regression and the $R^2$ values close to one. There is a spread in the component scores ($t_1$ and $t_2$), but there is a clustering of the position related data.

Figure 5:
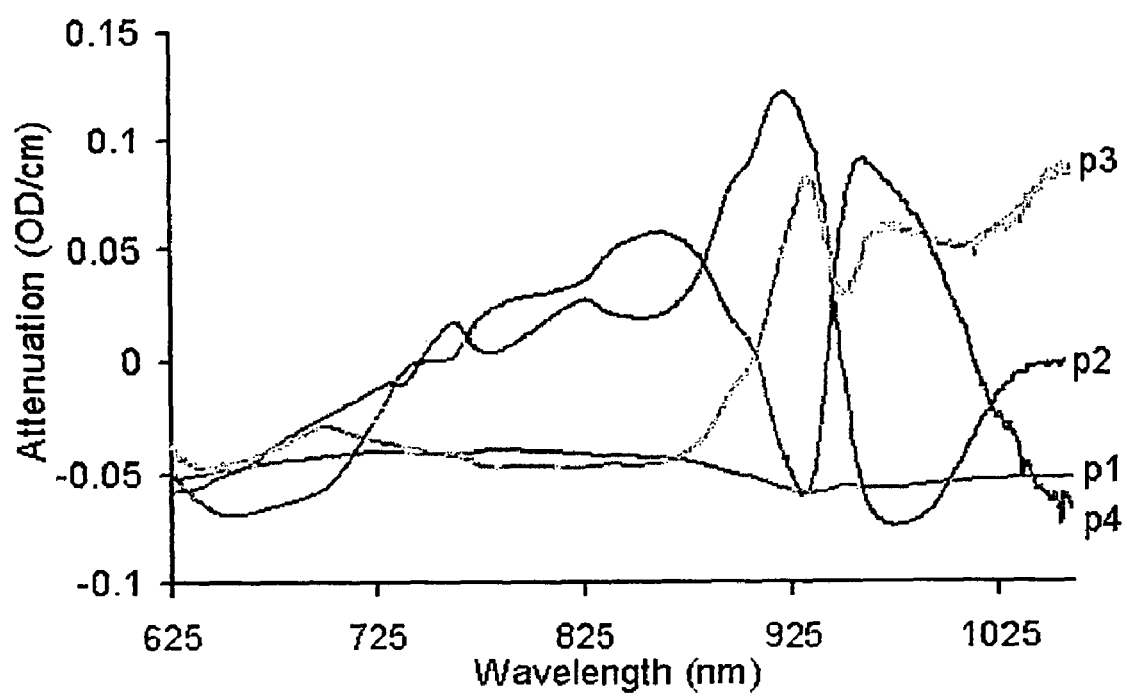
FIG. 5 showing the first 4 components obtained from the PCA following data pre-processing which included thickness and transfer function correction, note that component 2 show inverse absorption for the lipid and water peaks respectively.
Figure 6:
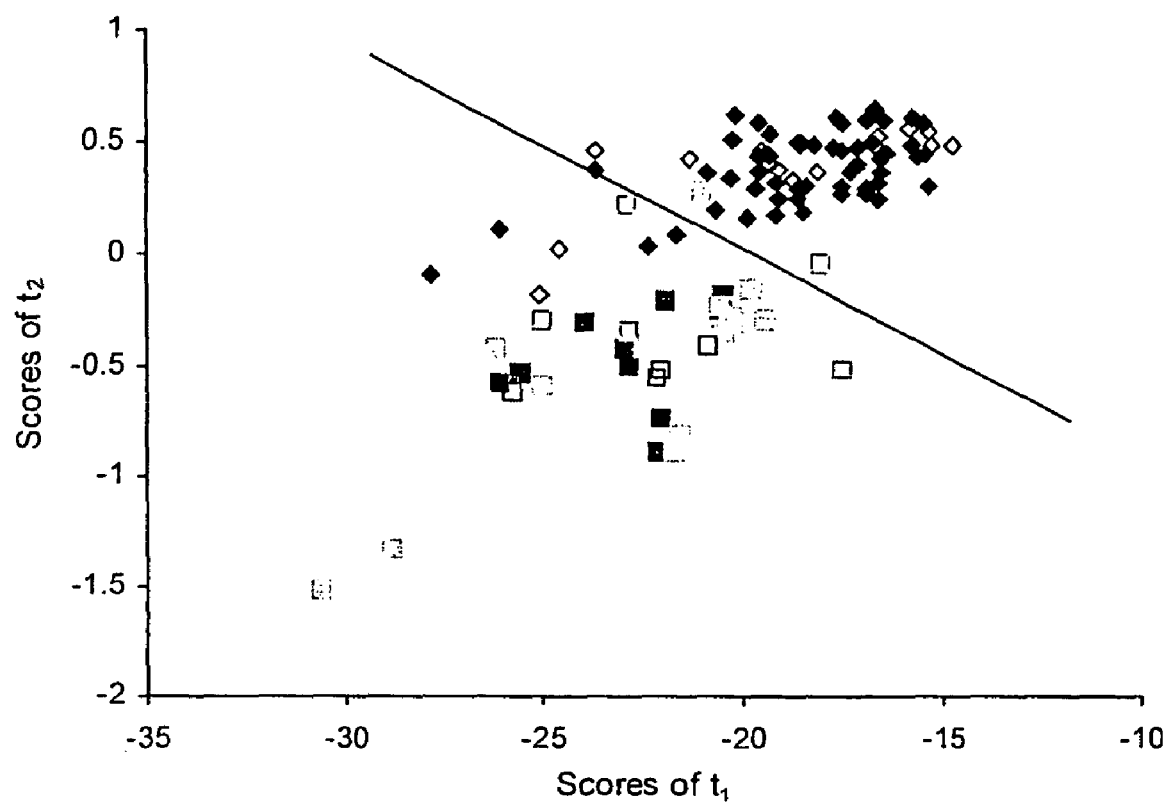
FIG. 6 shows the resulting weights or loading factors $t_1$ vs. $t_2$ for the first 2 principle components for thickness and transfer function correction as pre-processing option, square and rhombus symbols represent high and low breast density subjects, respectively.

FIG. 5 shows the principal components ($p_i$) from the PCA using n=544 spectra (thickness and transfer function corrected) obtained to date. These first four components contain 97.6%, 1.2%, 0.6% and 0.3% of the variance in the total data set, respectively, for a combined total of 99.8% of the variance. The cluster plot of the scores for $t_1$ and $t_2$ is shown in FIG. 6. This plot illustrates discrimination of the breast tissue areas across a diagonal line in the $t_1$ vs. $t_2$ space.

Figure 7:
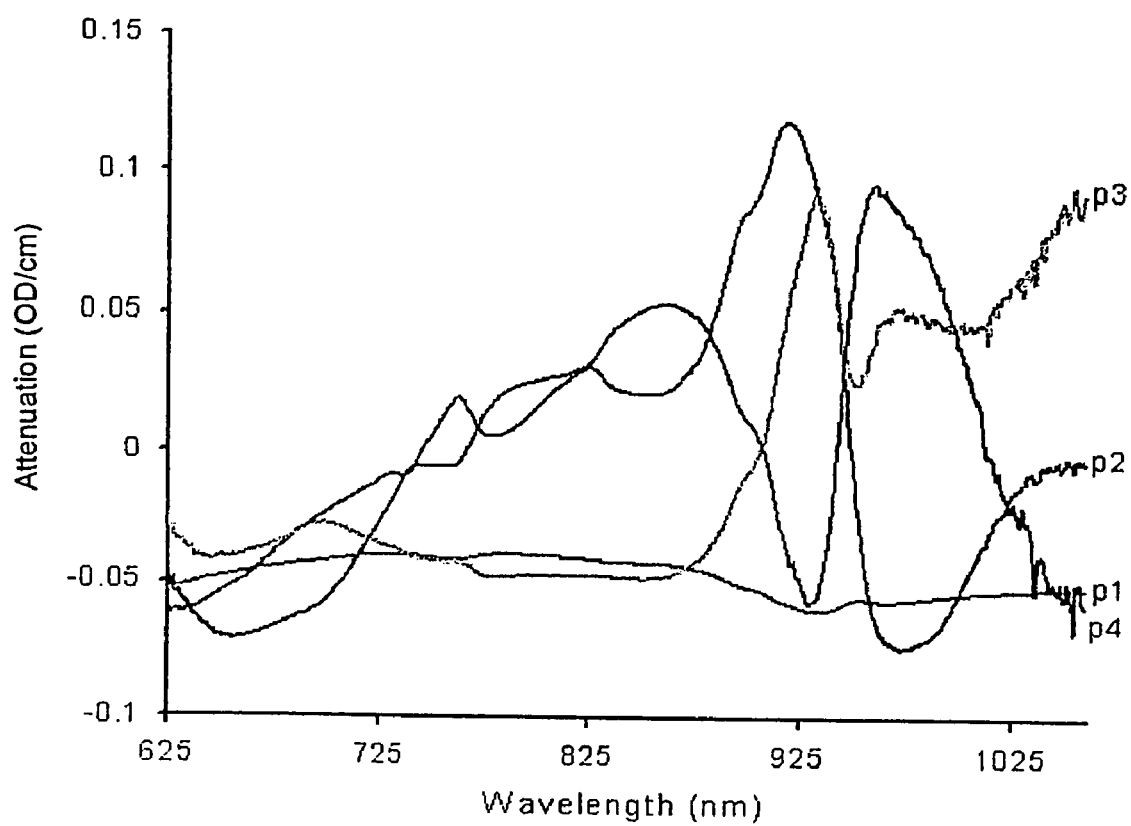
FIG. 7 shows the first four components obtained from the PCA following data pre-processing which includes only transfer function correction.

Non-thickness corrected spectra were used to determine the effect of thickness on the robustness of the PCA model prediction. The component spectra for $p_1$-$p_4$ are very similar to the thickness-corrected component plot; see FIGS. 5 and 7 respectively. The $t_1$ vs. $t_2$ plot, FIG. 8, for this data shows discrimination as a function of $t_2$ only. Similarly component spectra can be seen in FIG. 9 for thickness and transfer function corrected data that were additionally autoscaled, with the $t_1$ vs. $t_2$ cluster plot shown in FIG. 10. The scores for both $t_1$ and $t_2$ are centered on zero as expected but show similar clusters as FIG. 8.

Figure 8:
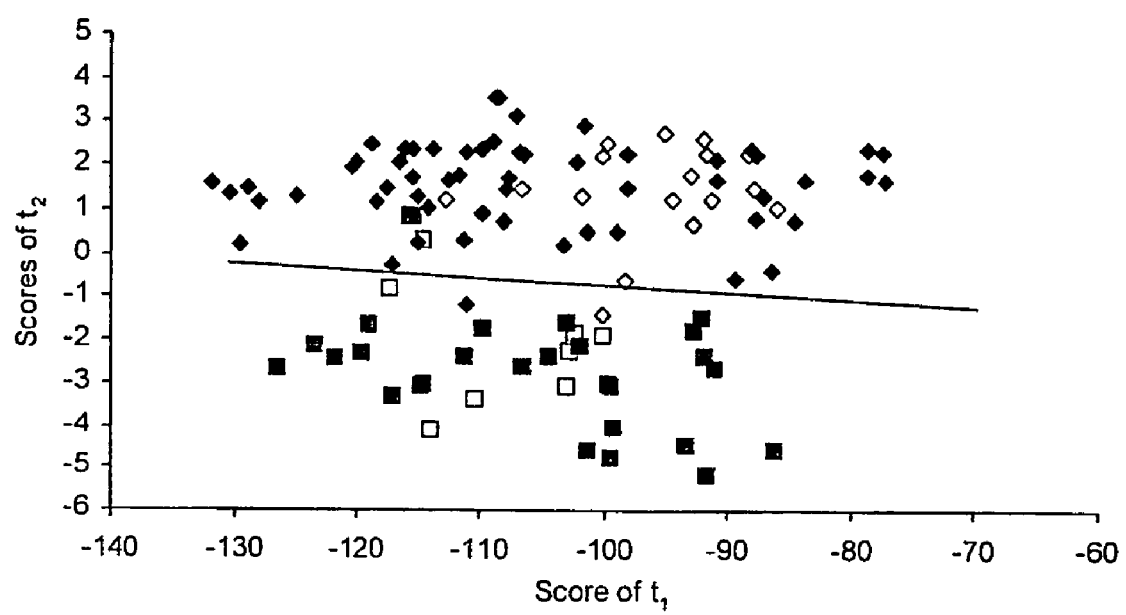
FIG. 8 shows the resulting weights or loading factors $t_1$ vs. $t_2$ for the first two principle components using transfer function correction as only pre-processing option, square and rhombus symbols represent high and low breast density subjects, respectively.
Figure 9:
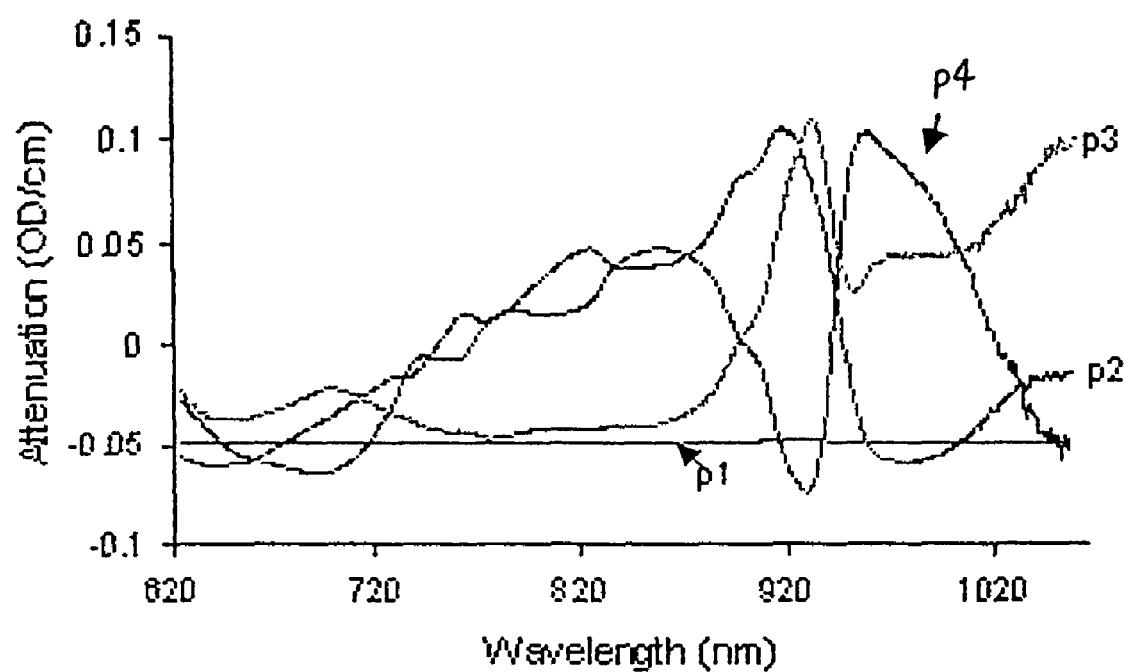
FIG. 9 shows the first 4 components obtained from the PCA following data pre-processing which includes thickness and transfer function correction followed by autoscaling of the data.
Figure 10:
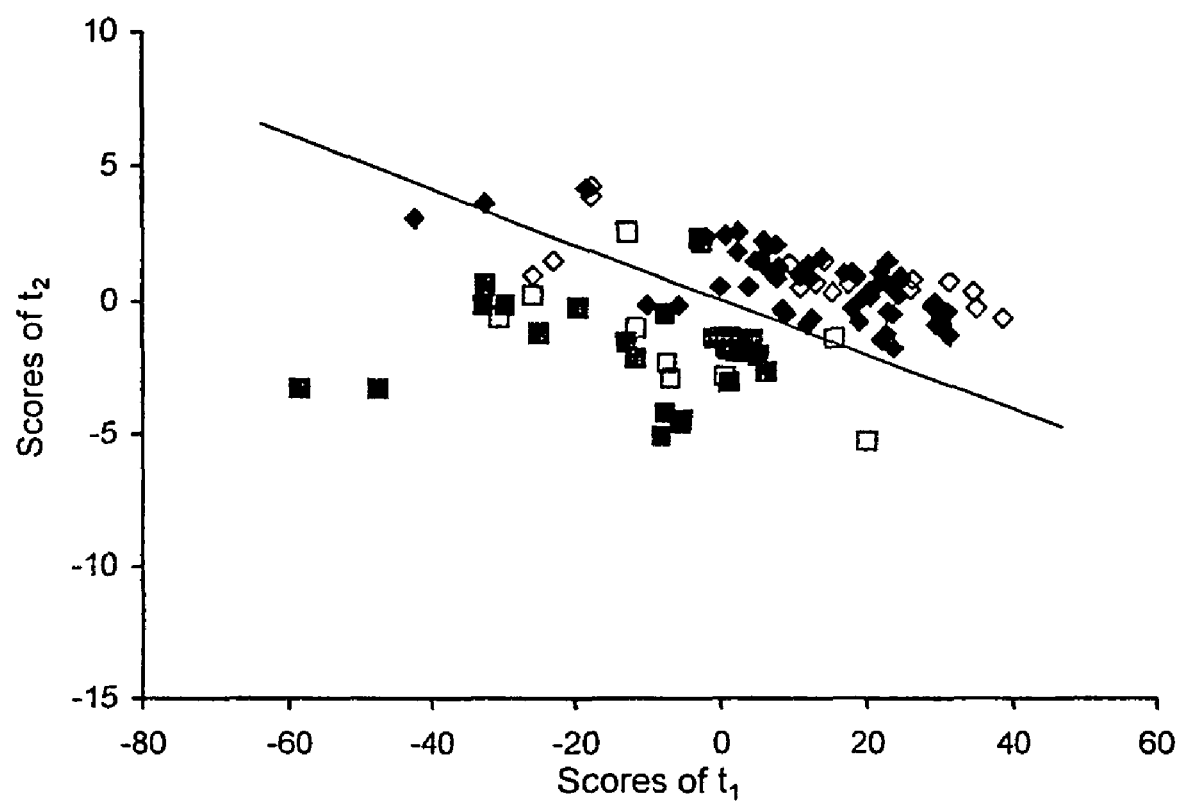
FIG. 10 shows the resulting weights or loading factors $t_1$ vs. $t_2$ for the first 2 principle components using thickness and transfer function correction followed by autoscaling of the data, square and rhombus symbols represent high and low breast density subjects, respectively.

HDM and LDM were determined to compare which spectral pre-processing option best differentiates the high and low density spectra in cluster plots according to FIGS. 6, 8 and 10. HDM and LDM data shown in the Table 4 were calculated from the same training and validation data sets separately.

TABLE 4

HDM and LDM of Principal Component Analysis results for test and validation set measurements.

| Pre-processing of Dataset | | Test set | | Validation Set | |
|---|---|---|---|---|---|
| | | HDM | LDM | HDM | LDM |
| Transfer function corrected (FIG. 8) | I | 85% | 97.0% | 88% | 90% |
| Thickness and transfer function corrected (FIG. 6) | II | 88% | 93% | 93% | 89% |
| Autoscaled - transfer function corrected (data not shown) | III | 86% | 94% | 90% | 86% |
| Autoscaled - thickness and transfer function corrected (FIG. 10) | IV | 87% | 92% | 93% | 90% |

Autoscaling removes some spectral information since the mean spectrum is wavelength dependent. As the spectral features contributing to the discrimination between high and low breast density or risk are unknown, losing spectral information is very unwise. This is reflected in a reduced HDM and LDM as seen in Table 4 for pre-processing option III and IV.

The scores $t_1$ and $t_2$ resulting from thickness corrected and non-corrected component spectra demonstrated that it is possible to differentiate between the subjects having low or high breast tissue density subjects (FIGS. 8 and 10).

While mathematical models derived for thickness or non-thickness corrected optical spectra differentiate high and low breast tissue densities, their $t_1$ vs. $t_2$ cluster plots differ. One explanation for the difference in the thickness corrected vs. non-corrected cluster plots is the effect of the physical tissue thickness on the overall variance within the spectral data set and therefore the determination of the components by the PCA algorithm. Thickness of the tissue contributes non-uniformly to individual spectra as larger breasts tend to contain more fatty tissue.

In the model of the data that was not thickness corrected, $p_1$ did not differentiate between high and low density tissue. This can also be seen in the magnitude of the $t_1$ in FIG. 5 versus the non-thickness corrected component spectra in FIG. 7. This indicates that the thickness values contribute to the magnitude of $p_1$ masking other contributions that do differentiate between tissue densities, such as light scattering. This leaves $t_2$ as the only component to preserve information to distinguish the density of the breast.

When comparing the autoscaled versus non-autoscaled data, there were minimal changes in the principal component spectra and minor differences in HDM and LDM values, see FIGS. 6 and 10 and Table 4. Autoscaling as part of the pre-processing can degrade regions with flat or extreme spectral variation. (14) In this case, degraded spectral features could include regions of the spectrum with minimal wavelength dependence and hence a first derivative close to zero. For example, the haemoglobin inflection points are more pronounced in the non-autoscaled data than in the autoscaled components. Conversely, the large spectral features of water and lipids are large compared to other structures in the spectra, but are less pronounced after autoscaling. In this study, the only differences in the HDM values are in the training set with the non-autoscaled data having almost 2% higher scores for both HDM and LDM.

Principal components can reveal particular regions of the spectrum that represent important physical properties or entities within the tissue that contribute to differentiation. Component spectra 1 ($p_1$) and 2 ($p_2$) are the most important cover the highest amount of variance in the data set. While components 3 and 4 have similar or inverse shape as component 2 they take less variance into account.

Principal component 1 ($p_1$) has a small dependence on wavelength and has negative values in each prepared model. The spectrally flat characteristics resulting from thickness corrected spectra can be attributed to attenuation due to absorption, scattering, and, therefore optical pathlength and losses at the tissue boundary. The surprisingly flat spectral shape of the scattering contribution is due to the derivation of OD used here, based on the wavelength dependent transfer function calibration by a polyurethane block which exhibits also high Mie scattering, e.g. Mie scattering is present in the spectrum and hence cancels itself out. We propose that $p_1$ carries optical pathlength information despite not showing the typical $\lambda^{-1}$ dependency, (18) but contains information to determine breast density through the overall scattering power. Low density tissue spectra have a reduced amount of scattering compared to high density tissue, and, therefore, higher values of $t_1$ in FIGS. 8 and 10. This relationship in scattering properties is also seen in the scattering coefficient data by Peters et al. (19) and Troy et al. (20) supporting this interpretation of the first principal component.

Figure 11:
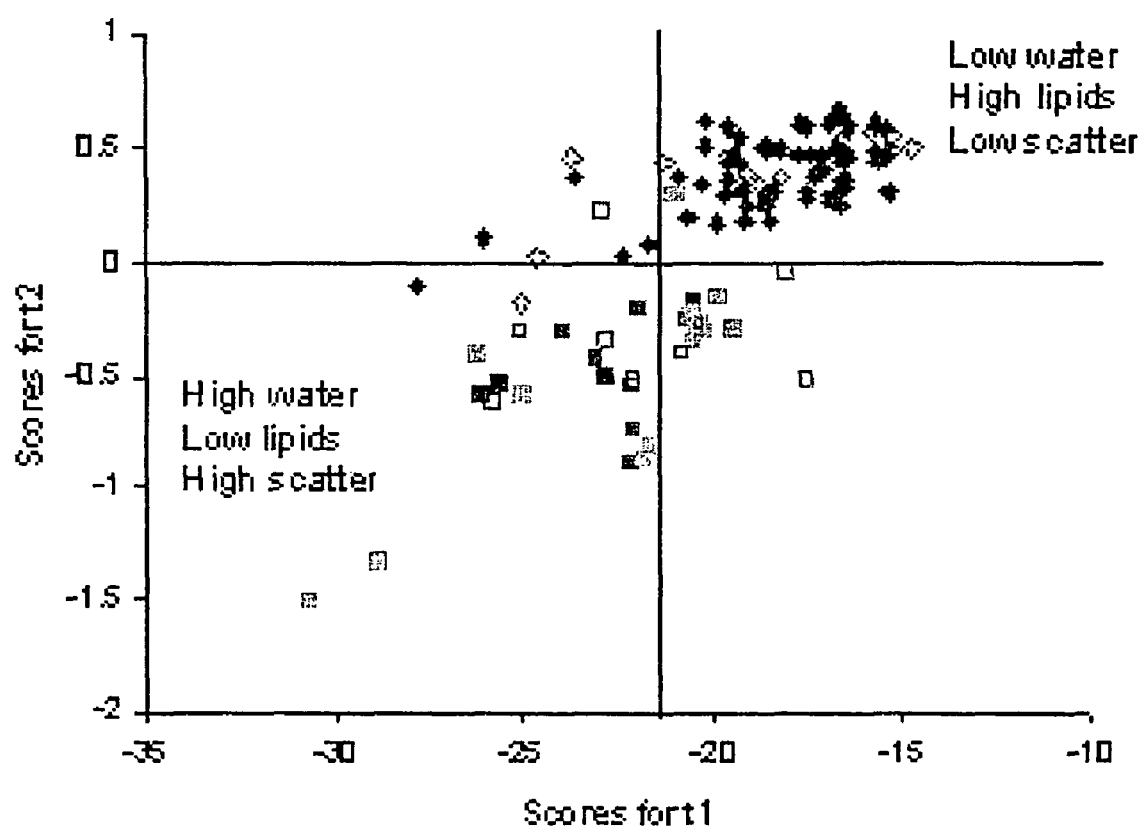
FIG. 11 assigns physical meaning to the four quadrants in the $t_1$ vs. $t_2$ plots, shown here for thickness and transfer function corrected and autoscaled data

The other component enabling differentiation between low and high tissue densities $p_2$, has a more complex shape when compared to $p_1$. The most important spectral features in the component are the lipid with inverse water peaks present at 930 nm and 980 nm, respectively. When t2 values are positive, the lipid peak is the dominant spectral feature as anticipated for fatty or low density tissue. Spectra from the high density tissue have negative t2 values and water absorption becomes the dominant structure in the component spectrum. Graham et al. (21) also observed this relationship between water and density values when using MRI to quantify percent density. In their study the water content of the tissue was measured directly and showed good correlation to percent tissue density (r=0.79). (21) Spectral feature contributions by haemoglobin can be seen between 625 and 850 nm within $p_2$ where the negative slope and inflection points of the haemoglobin curve are apparent. Dense breast tissue has large negative scores ($t_2$) compared to the low density tissue. Haemoglobin contributes to the variance in $p_2$, with elevated contribution of blood related absorption for high water absorption seen in the higher density tissue. This simultaneous appearance of water and haemoglobin absorption can be explained physiologically, as tissues with higher water content and hence cellular content, require improved vascular supply and, thereby, increased blood volume. (22) Since positive $t_2$ scores are related to low tissue density and positive $t_1$ scores are related to low tissue scatter, the cluster plot of t1 and t2 can be divided into quadrants as shown in FIG. 11, highlighting the relationship between the spectral features and the known physical attributes of the breast tissue.

Figure 12:
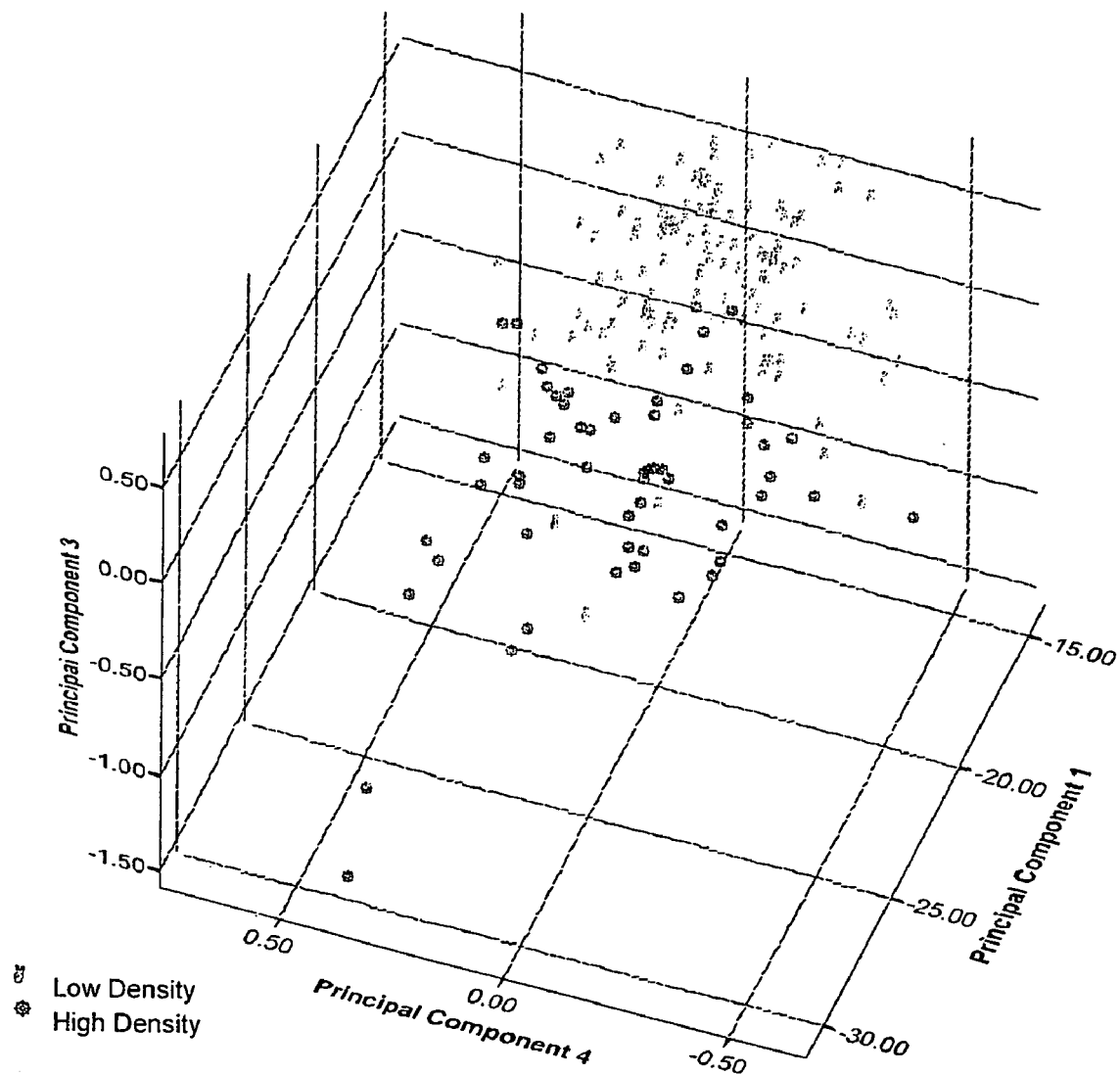
FIG. 12 shows an identification of spectra form low and high density breast-tissue within a 3D plot of $t_1$ vs. $t_2$ and $t_3$ using thickness and transfer function correction as pre-processing options.

Even though p3 and p4 did not show differentiation between high and low density tissue by themselves in a 2-dimensional plot like p1 and p2, areas of the component spectra can be interpreted. Additionally p3 shows a lipid absorption peak, but water and hemoglobin absorption are almost absent additionally the lipid peak is shifted towards longer wavelength, so the reason therefore is unknown. p4 shows influence from the hemoglobin, with the same slope but inverse inflection points to p2. Even though differences in the amplitude and general shape of the curves are minimal when compared to p2 the magnitude of the scores t3 and t4 are much smaller than that of the first two components. One cannot exclude specifically p4 as a third contributor to increase HDM and LDM when using a three dimensional analysis as suggested in FIG. 12.

Figure 13:
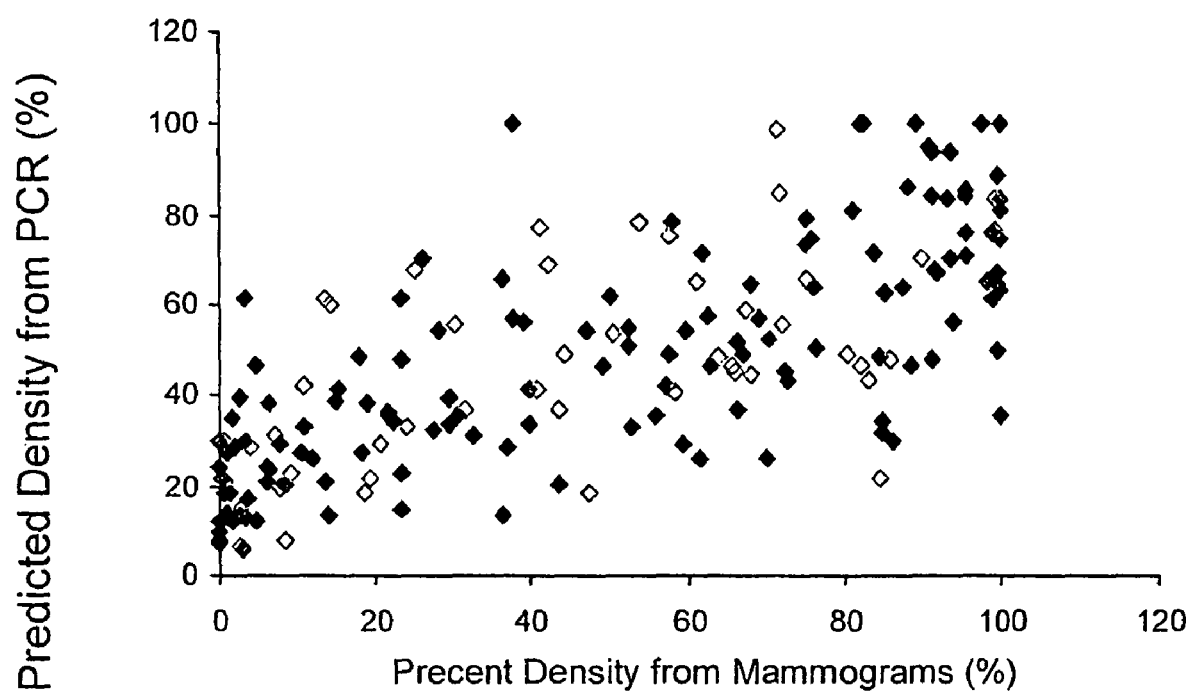
FIG. 13 shows the predicted % parenchymal tissue density based on PLS analysis of the optical transillumination spectra versus percent density according computer assisted analysis of the mammograms, solid symbols refer to the training set and open symbols to the validation set.

FIG. 13 shows an example of representing the parenchymal tissue density on an interval scale (% dense area in the mammogram) rather than a nominal scale (low, medium, high density). The % dense area can be determined using a computer assisted imaging program by a trained observer such as for example a radiologist. In the case presented here no trained person was utilized and hence the percent density from the mammograms contained a large error in the repeat measure which ultimately limits the accuracy of the presented correlation. However, it serves to indicate that the variance reduction programs employed are capable of providing a single integer number to the physician monitoring his patients' health.

The results disclosed herein show that In vivo optical transillumination spectroscopy is a technically feasible method and capable of predicting breast tissue densities with acceptable correlation to mammographic densities as an indirect method of cancer risk assessment. Thus, transillumination spectroscopy may offer a novel "first step" in the risk assessment of healthy women regardless of menstrual cycle, age, ethnic background or menopausal status as the data here was not stratified by either event.

HDM and LDM values close to or above 90% are encouraging to distinguish between low and high density tissues. These HDM and LDM values are higher compared with other physical examinations, such as ultrasound (23) and magnetic resonance imaging, (21) reported to be between 70-80%.

Optical transillumination spectroscopy offers the potential of a real-time and cost-effective method compared with ultrasound and has the ability to quantify a large range of tissue densities for breasts that are up to 6 cm in thickness. An added advantage of transillumination spectroscopy over ultrasound and MRI is the fact that results are derived from preset mathematical models and, hence, no additional highly trained personnel are required for assessment. This reduces the overall cost to the healthcare system for this risk-assessment technique. A painless procedure and the inherent safety of this method will likely contribute to a high compliance rate.

X-ray mammography uses ionizing radiation and is considered unacceptable as a tool to assess breast density for women less than forty years of age and for frequent measurement. However, transillumination spectroscopy is safe for women of all ages. This allows risk assessment to commence at a much younger age when the life style and diet are perhaps easier to influence have more time to exert their beneficial effects to reduce the risk and could ultimately lead to reduced incidence rates.

While optical transillumination spectroscopy is a promising tool to monitor the effectiveness of chemopreventive, dietary or lifestyle studies for the reduction of breast cancer risk, its ability to detect physical changes over a period of time in the breast tissue of a given individual needs to be demonstrated in a prospective longitudinal study.

The predictive value of optical spectroscopy for disease susceptibility quantification can be increased through additional measurements which can include extending the optical waveband, obtain optical information of interrogated tissue not contributing to the disease risk and obtaining information separately for light scattering.

The first option includes the use of wavelength up to 1.7 μm which contain among others additional water and lipid absorption bands using an InGaAs based opto-electronic detector or an equivalent system. This is particular of interest for large tissue volumes. If the optically interrogated tissue volume is small, that is in the range of several $mm^3$, the short wavelength band using light of approximately 360 nm to 600 nm may provide the relevant information.

Figure 14:
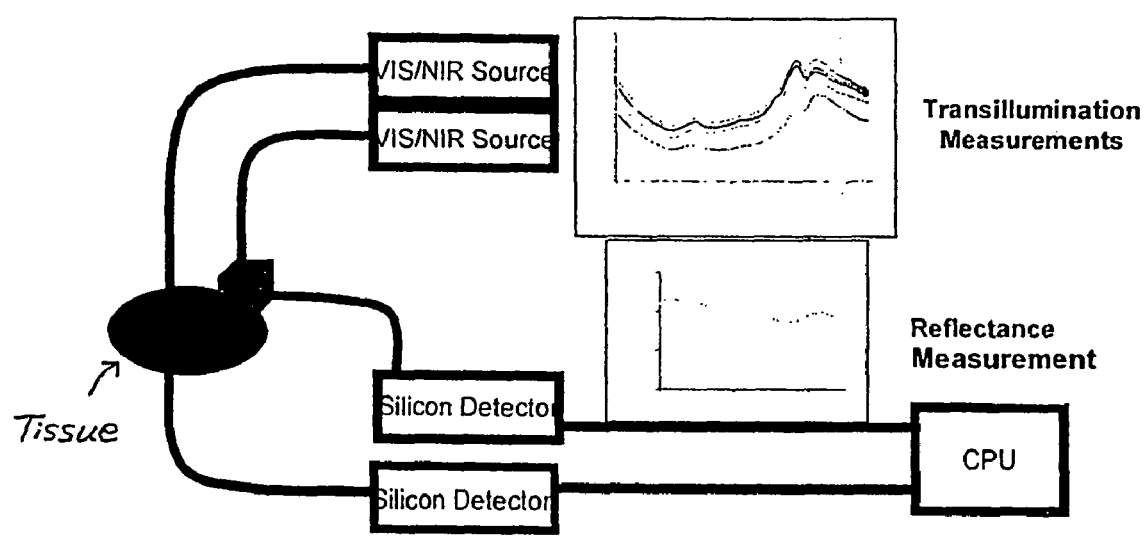
FIG. 14 shows spectrally resolved transillumination and reflectance measurements are obtained by the used of one of more appropriate VIS/NIR light sources and opto-electronic detector systems measuring the surface proximal volume layer and the total volume separately.

For the second option, using a combined transmittance and reflectance measurement as shown in FIG. 14 enables collection of the optical information related to the superficial tissue, here skin, separately through the reflectance technique, whereas the transillumination spectroscopy contain information about the superficial and deep tissue.

Figure 15:
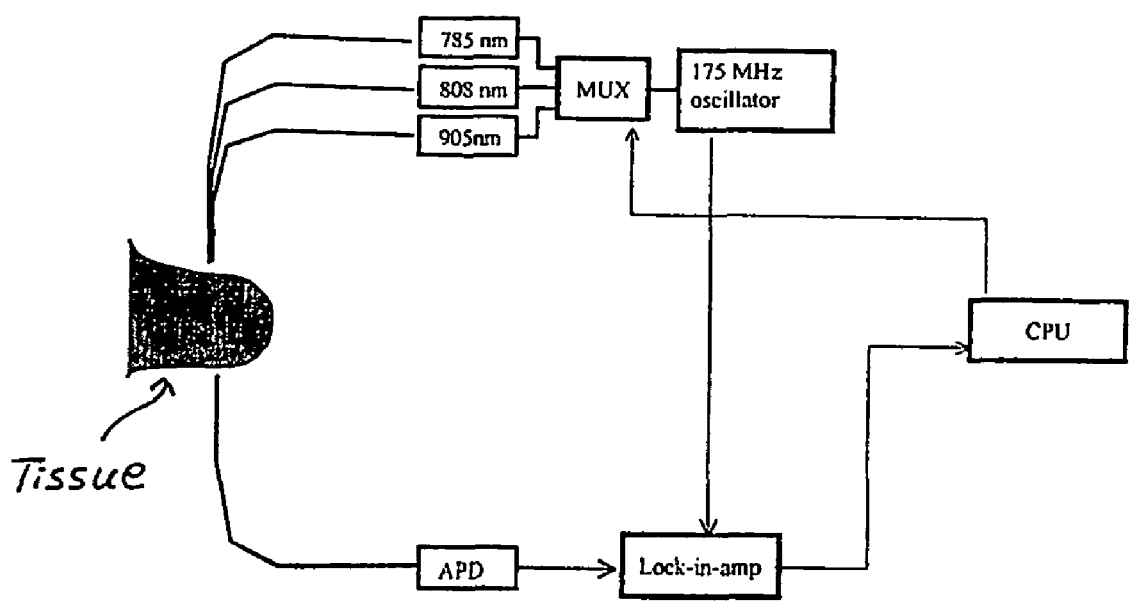
FIG. 15 shows an example of a three wavelength frequency domain system to determine the differential path-length factor of photons traversing tissue.

As described above frequency or time domain reflectance and transillumination measurements can provide an effective optical path length through phase shift or lifetime measurements. The optical path length relative to the physical path length between the optodes is related to the light scattering power of the tissue. FIG. 15 shows an example of an embodiment of a system comprised of three diode lasers to measure the breast tissue light scattering power. The remaining part of the spectrum can be interpolated as shown in the paper by Cerussi et al (24).

The present method and apparatus disclosed herein has been exemplified using breast cancer as the disease of interest which involves correlating the associated scalar coefficient of the basis spectral component(s) with the pre-selected property of parenchymal breast tissue density known to be indicative of susceptibility of breast tissue for breast cancer.

It will however be understood that this invention is not restricted to use in assessing risk for breast cancer but many other diseases as well. For example, the method disclosed herein is contemplated to be applicable for correlating optical information of other mammalian tissue with risk factors associated with diseases such as neurodegenerative diseases including Multiple Sclerosis, Alzheimer's and Parkihson's diseases; oncology including, prostate, rectal and testicular cancers, autoimmune diseases including Sinustisus, rheumatoid arthritis, and Chron's disease. In each case the relevant tissues are optically sampled and the basis spectral component(s) are obtained using other techniques such as ultrasound, X-ray analysis, magnetic resonance imaging, potential molecular markers indicating initial changes in the tissue, or epidemiologically derived questionnaires proven to correlate with the disease of interest as just a couple of examples.

The present invention is applicable to mammals in general and is not restricted to humans.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. Boyd N F. Lockwood G A. Martin L J. Knight J A. Jong R A. Fishell E. Byng J W. Yaffe M J. Tritchler D L. Mammographic densities and risk of breast cancer among subjects with a family history of this disease. Journal of the National Cancer Institute. 91(16):1404-8, 1999
2. Boyd N F. Lockwood G A. Byng J W. Tritchler D L. Yaffe M J. Mammographic densities and breast cancer risk. Cancer Epidemiology, Biomarkers & Prevention. 7(12): 1133-44, 1998
3. Byng J W. Yaffe M J. Jong R A. Shumak R S. Lockwood G A. Tritchler D L. Boyd N F. Analysis of mammographic density and breast cancer risk from digitized mammograms. Radiographics. 18(6):1587-98, 1998
4. Knight J A. Martin L J. Greenberg. C V. Lockwood G A. Byng J W. Yaffe M J. Tritchler D L. Boyd N F. Macronutrient intake and change in mammographic density at menopause: results from a randomized trial. Cancer Epidemiology, Biomarkers & Prevention. 8(2):123-8, 1999
5. Zhu Q. Conant E. Chance B. Optical imaging as an adjunct to sonograph in differentiating benign from malignant breast lesions Journal of Biomedical Optics. 5(2):229-36, 2000
6. Franceschini M A. Moesta K T. Fantini S. Gaida G. Gratton E. Jess H. Mantulin W W. Seeber M. Schlag P M. Kaschke M. Frequency-domain techniques enhance optical mammography: initial clinical results. Proceedings of the National Academy of Sciences of the United States of America. 94(12):6468-73, 1997
7. Quaresima V. Matcher S J. Ferrari M. Identification and quantification of intrinsic optical contrast for near-infrared mammography. Photochemistry & Photobiology. 67(1):4-14, 1998
8. Egan and Dolen Optical spectroscopy. Pre-mammography marker. Acta Radiologica. 29(5): 497-503, 1988
9. Thompson and Tatman Physiological and pathological factors of human breast disease that can influence optical diagnosis. Ann New York Acad Scie 838:171-93 1998
10. Gratton E. Fantini S. Franceschini M A. Gratton G. Fabiani M. Measurements of scattering and absorption changes in muscle and brain. Philosophical Transactions of the Royal Society of London—Series B: Biological Sciences. 352:727-35, 1997
11. Jacques S L. Path integral description of light transport in tissue. Annals of the New York Academy of Sciences. 838:1-13, 1998

12. Berger, A. J., Koo, T-W., Itzkan, I., & Feld, M. S. 1998, 'An Enhanced Algorithm for Linear Multivariate Calibration' Analytical Chemistry, vol. 70(3), pp. 623-627.
13. Haaland D M and Thomas E V., Partial Least-Squares Methods for Spectral Analysis. 1. Relation to Other Quantitative Calibration Methods and the Extraction of Qualitative Information *Anal. Chem.* 60 1193-1202, 1988
14. Haaland D M and Thomas E V., Partial Least-Squares Methods for Spectral Analysis. 2. Application to Simulated and Glass Spectral Data *Anal. Chem.* 60 1202-1208, 1988
15. Wise B M., PLS Toolbox Tutorial: Matlab Version 6. Eigenvector Research Inc. 2000
16. Balakrishnama S, Ganaphthiraju A. Linear Discriminant Analysis: A Brief Tutorial Institute for Signal and Information Processing Mississippi State University 2001
17. Kowalski B R and Geladi P., Partial Least-Squares Regression: A Tutorial. Analytica Chimica Acta 185: 1-17, 1986
18. Welch A J and van Gemert M J C (Editors) Optical-Thermal Response of Laser-Irradiated Tissue. Plenum Press New York, USA. 1995
19. Peters J, Patterson M S, Wilson B C, Optical properties of normal and diseased human breast tissues in the visible and near infrared. *Phys Med Biol,* 35:1317-1334, 1990
20. Troy T, Page D L, Sevick-Muraca E M., Optical Properties of Normal and Diseased Breast Tissues: Prognosis for Optical Mammography. *Biomedical Optical Spectroscopy and Diagnostics* J Opt Soc Am, 3: 59-66, 1996
21. Graham S J, Bronskill M J, Byng J W, Yaffe M J, Boyd N F., Quantitative correlation of breast tissue parameters using magnetic resonance and X-ray mammography. *Br J Cancer;* 73(2):162-8, 1996
22. Haskell R C, Svaasand L O, Tsay T T, Feng T C, McAdams M S, Tromberg B J., Boundary conditions for the diffusion equation in radiative transfer. J Opt Soc Am A 11: 2727-41, 1994
23; Kaizer L, Fishell E K, Hunt J W, Foster F S, Boyd N F. Ultrasonographically defined parenchymal patterns of the breast relationship to mammographic patterns and other risk factors for breast cancer. *Br J Radiol.* 61(722): 118-24, 1988
24. Cerussi A E, Berger A J, Bevilacqua F, Shah N, Jakubowski D, Butler J, Holcombe R F, Tromberg B J, Sources of Absorption ans Scattering contrast for near-infrared optical mammography. *Acad Rdiol* 8:211-218: 2001

Therefore what is claimed is:

1. A method for assessing susceptibility for developing a pre-selected disease in a mammal, comprising:
    a) illuminating a volume of selected tissue of a mammal with light having wavelengths covering a pre-selected spectral range;
    b) detecting light transmitted through, or reflected from, said volume of selected tissue, and obtaining a spectrum of said detected light;
    c) representing the spectrum of detected light by a set of basis spectral components, an error term, and an associated scalar coefficient for each basis spectral component in said set, the set of basis spectral components including at least one basis spectral component, the associated scalar coefficient for each basis spectral component being calculated by minimizing the error term; and
    d) correlating the associated scalar coefficient for each basis spectral component with a pre-selected property of the selected tissue known to be indicative of susceptibility of the tissue for the pre-selected disease to obtain the susceptibility for the mammal to developing the pre-selected disease:
    wherein the set of basis spectral components of step (c) is obtained by the steps of:
        obtaining a range of values of the pre-selected property from a population cross section which is representative of the mammalian population at large, but who are not expressing the pre-selected disease;
        in each mammalian member of said population cross section obtaining at least one spectrum by illuminating a volume of selected tissue with light having wavelengths covering the pre-selected spectral range, and detecting light transmitted through, or reflected from, said volume of selected tissue;
        extracting common spectral elements from the at least one spectrum of each member of said population cross section and producing at least one set of component spectra from the extracted common spectral elements, the at least one set of component spectra including at least one component spectra; and
        identifying a set of component spectra which gives the highest predictive value for the pre-selected property of the selected tissue known to be indicative of susceptibility for the pre-selected disease;
        wherein said set of component spectra which gives the highest predictive value for the pre-selected property of the selected tissue known to be indicative of susceptibility for the pre-selected disease is used as the set of basis spectral components in step c).

2. The method according to claim 1 wherein the step of extracting common spectral elements from the at least one spectrum of each member of said population cross section and producing at least one set of component spectra from the extracted common spectral elements includes using one of Principle Component Analysis, Partial Least Squares and Principle Component Regression.

3. The method according to claim 1 wherein the step of calculating the associated scalar coefficient by minimizing the error term includes using Chi-square fitting to minimize the error term.

4. The method according to claim 1 including repeating steps a) to d) inclusively for a particular mammal periodically over a pre-selected period of the mammal's lifetime and storing the susceptibilities calculated periodically to detect a rate of change in susceptibility for increased risk for the pre-selected disease.

5. The method according to claim 1 wherein said mammal is a post puberty human female, and wherein the pre-selected disease is breast cancer, and the pre-selected property is parenchymal breast tissue density.

6. The method according to claim 5 wherein the parenchymal breast tissue density is measured by one of x-ray mammography, ultrasound, computed tomography, cone beam computed tomography, electrical impedance spectroscopy and magnetic resonance imaging.

7. The method according to claim 1 wherein the spectrum of said detected light is a continuous spectrum.

8. The method according to claim 1 wherein the spectrum of said detected light is a discrete spectrum.

9. The method according to claim 1 wherein the step of illuminating a volume of selected tissue of a mammal with light having wavelengths covering a pre-selected spectral range includes illuminating with broad band light, discrete wavelengths or wavelength bands.

10. The method according to claim 1 wherein the steps of illuminating a volume of selected tissue and detecting light transmitted through, or reflected from, said volume of selected tissue includes adjusting an angle and a distance between a position on the tissue surface which is illuminated and a position on the tissue surface where the transmitted or reflected light emanates from which is detected.

11. The method according to claim 1 wherein said pre-selected disease is selected from the group consisting of neurodegenerative diseases, oncology based diseases and autoimmune diseases.

12. The method according to claim 11 wherein said neurodegenerative diseases include Multiple Sclerosis, Alzheimer's and Parkinson's disease, and wherein said oncology based diseases include prostate, rectal and testicular cancers, and wherein said autoimmune diseases include sinustisus, rheumatoid arthritis, and Crohn's disease.

13. The method according to claim 1 wherein the set of basis spectral components includes two or more component spectra.

14. The method according to claim 1 wherein step d) includes using an effective mathematical variance reduction model to identify the basis spectral components which through the associated scalar coefficient shows best correlation with the pre-selected property of the selected tissue known to be indicative of susceptibility of the tissue for the pre-selected disease.

15. An apparatus for optical assessing susceptibility for developing a pre-selected disease in a mammal, comprising:
   a) holder means for holding and immobilizing an anatomical part of a mammal containing tissue to be optically probed;
   b) light source means for illuminating a volume of selected tissue of a mammal with light having wavelengths covering a pre-selected spectral range;
   c) detection means for detecting light transmitted through, or reflected from, said volume of selected tissue;
   d) computer control means connected to said detection means for producing a spectrum of said detected light from an output of said detection means, the computer control means including processing means for representing the spectrum of detected light by a set of basis spectral components, an error term, and an associated scalar coefficient for each spectral component in said set, the set of basis spectral components including at least one basis spectral component, the associated scalar coefficient for each basis spectral component being calculated by minimizing the error term, the processing means includes means for correlating the associated scalar coefficient for each basis spectral component with a pre-selected property of the selected tissue known to be indicative of susceptibility of the tissue for the pre-selected disease to obtain the susceptibility for the mammal to developing the pre-selected disease, the computer control means including display means for displaying the susceptibility.

16. The apparatus according to claim 15 wherein the at least one basis spectral component is obtained by the steps of obtaining a range of values of the pre-selected property from a population cross section which is representative of the mammalian population at large, but who are not expressing the pre-selected disease;
   in each mammalian member of said population cross section obtaining at least one spectrum by illuminating a volume of selected tissue with light having wavelengths covering the pre-selected spectral range, and detecting light transmitted through, or reflected from, said volume of selected tissue;
   extracting common spectral elements from the at least one spectrum of each member of said population cross section and producing at least one set of component spectra from the extracted common spectral elements, the at least one set of component spectra including at least one component spectra;
   identifying a set of component spectra which gives the highest predictive value for the pre-selected property of the selected tissue known to be indicative of susceptibility for the pre-selected disease; and
   using said set of component spectra which gives the highest predictive value for the pre-selected property of the selected tissue known to be indicative of susceptibility for the pre-selected disease as the set of basis spectral components in claim 15.

17. The apparatus according to claim 15 wherein the light source means includes either one of a white light source such as a filtered halogen lamp, a series of bandwidth limited light emitting diodes (LEDs), several laser light sources all emitting within the pre-selected spectral range.

18. The apparatus according to claim 15 wherein the detection means includes either wavelength selective means in conjunction with a charge coupled device or a photodiode array all for parallel detection of the pre-selected wavelength band or an avalanche photodiode or point photo detector for sequential detection of the pre-selected wavelength band.

19. The apparatus according to claim 15 wherein the processing means includes calibration means for measuring a wavelength dependent instrument transfer function, and wherein said processing means includes means for removing instrumental affects on the spectrum of detected light.

20. The apparatus according to claim 18 wherein the calibration means for measuring a wavelength dependent instrument transfer function includes a pre-selected volume of material which preferentially scatters light rather than absorbing light, positioned in place of the pre-selected tissue.

21. The apparatus according to claim 20 wherein the material which preferentially scatters light rather than absorbing light is comprised of highly density poly-urethane.

22. The apparatus according to claim 15 wherein said detection means is positioned to detect light reflected from the tissue being illuminated, including means for adjusting the angle and distance between the light source means and the detection means.

23. The apparatus according to claim 15 wherein the light source means includes a light source and an optical fiber with a proximal end positioned to couple light into said optical fiber and a distal end from which light emanates from the fiber positioned so as to direct light onto the pre-selected tissue.

24. The apparatus according to claim 15 wherein the mammal is a post puberty human female, and wherein the pre-selected disease is breast cancer, and wherein the holder means includes a breast support including at least one illumination means and at least one detection means for each breast.

* * * * *